United States Patent
Kim et al.

(10) Patent No.: US 9,650,419 B2
(45) Date of Patent: May 16, 2017

(54) BIOCOMPATIBLE PROTEIN, BIOCOMPATIBLE PROTEIN GEL AND BIOCOMPATIBLE CONDUCTING PROTEIN GEL COMPRISING THE PROTEIN AND METHOD FOR PREPARING THE SAME

(71) Applicant: Research & Business Foundation SUNGKYUNKWAN UNIVERSITY, Suwon-si (KR)

(72) Inventors: Yongho Kim, Suwon-si (KR); Yong Tae Kim, Suwon-si (KR); Kook-han Kim, Seoul (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 14/811,350

(22) Filed: Jul. 28, 2015

(65) Prior Publication Data
US 2016/0024154 A1    Jan. 28, 2016

(30) Foreign Application Priority Data

Jul. 28, 2014    (KR) .................. 10-2014-0095512
Feb. 2, 2015    (KR) .................. 10-2015-0016171

(51) Int. Cl.
| | |
|---|---|
| *C07K 7/08* | (2006.01) |
| *A61K 33/00* | (2006.01) |
| *A61K 38/10* | (2006.01) |
| *B82Y 5/00* | (2011.01) |
| *A61L 27/22* | (2006.01) |
| *A61L 27/44* | (2006.01) |
| *A61K 47/42* | (2017.01) |
| *A61K 38/00* | (2006.01) |

(52) U.S. Cl.
CPC .............. *C07K 7/08* (2013.01); *A61K 38/10* (2013.01); *A61L 27/227* (2013.01); *A61L 27/443* (2013.01); *B82Y 5/00* (2013.01); *A61K 38/00* (2013.01); *A61K 47/42* (2013.01); *A61L 2430/00* (2013.01)

(58) Field of Classification Search
None
See application file for complete search history.

(56) References Cited

U.S. PATENT DOCUMENTS

2007/0243255 A1    10/2007    Xu et al.

FOREIGN PATENT DOCUMENTS

WO    WO 2010/045342 A1    4/2010

OTHER PUBLICATIONS

"The 20 Amino Acids," available at http://www.proteinstructures.com/Structure/Structure/amino-acids.html, 2 pages, accessed on Nov. 23, 2016, 9:57:49 AM.*
"Hydrophobic amino acids," available at http://www.russelllab.org/aas/hydrophobic.html, 2 pages, accessed on Nov. 23, 2016, 9:23:36 AM.*
"Amino Acids Reference Chart," available at http://www.sigmaaldrich.com/life-science/metabolomics/learning-center/amino-acid-reference-chart.html, 3 pages, accessed on Nov. 23, 2016, 9:41:31 AM.*
Korean Office Action issued in counterpart Korean Application No. 10-2015-0016171 on Apr. 15, 2015 (5 Pages in Korean).
Yang, Zhimou, et al. "In Vitro and In Vivo Enzymatic Formation of Supramolecular Hydrogels Based on Self-Assembled Nanofibers of a β-Amino Acid Derivative." Small 3.4 (2007):558-562.
Kim, Taek Gyoung, et al. "Biomimetic scaffolds for tissue engineering." Advanced Functional Materials 22.12 (2012):2446-2468.

* cited by examiner

*Primary Examiner* — Marcela M Cordero Garcia
*Assistant Examiner* — Catherine Mader
(74) *Attorney, Agent, or Firm* — NSIP Law

(57) ABSTRACT

Provided herein is a biocompatible protein, and biocompatible protein gel and conductive protein gel including the biocompatible protein, and preparing method thereof, the amino acid sequence of the biocompatible protein being Lys-X-Lys-Glu-X-Phe-Phe-X-Lys-Glu-X-Phe-Phe-X-Lys-Glu-X-Tyr, X being any one or more of hydrophobic amino acids, and the method including synthesizing a protein that causes no rejections from human bodies and that is not easily degradable, thereby providing an advantage of being utilized as a conductive biomaterial having biocompatibility and biodegradability in regenerative medical fields such as 3D bioprinting.

17 Claims, 8 Drawing Sheets

SEQUENCE LISTING

```
<160> NUMBER OF SEQ ID NOS: 28

<210> SEQ ID NO 1
<211> LENGTH: 12
<212> TYPE: PRT
<213> ORGANISM: Artificial Sequence
<220> FEATURE:
<223> OTHER INFORMATION: synthetic construct

<400> SEQUENCE: 1

Lys Val Lys Glu Val Phe Phe Val Lys Glu Val Tyr
1               5                   10

<210> SEQ ID NO 2
<211> LENGTH: 18
<212> TYPE: PRT
<213> ORGANISM: Artificial Sequence
<220> FEATURE:
<223> OTHER INFORMATION: synthetic construct

<400> SEQUENCE: 2

Lys Val Lys Glu Val Phe Phe Val Lys Glu Val Phe Phe Val Lys Glu
1               5                   10                  15

Val Tyr

<210> SEQ ID NO 3
<211> LENGTH: 18
<212> TYPE: PRT
<213> ORGANISM: Artificial Sequence
<220> FEATURE:
<223> OTHER INFORMATION: synthetic construct

<400> SEQUENCE: 3

Lys Leu Lys Glu Leu Phe Phe Leu Lys Glu Leu Phe Phe Leu Lys Glu
1               5                   10                  15

Leu Tyr

<210> SEQ ID NO 4
<211> LENGTH: 18
<212> TYPE: PRT
```

```
<213> ORGANISM: Artificial Sequence
<220> FEATURE:
<223> OTHER INFORMATION: synthetic construct

<400> SEQUENCE: 4

Lys Ala Lys Glu Ala Phe Phe Ala Lys Glu Ala Phe Phe Ala Lys Glu
1               5                   10                  15

Ala Tyr

<210> SEQ ID NO 5
<211> LENGTH: 18
<212> TYPE: PRT
<213> ORGANISM: Artificial Sequence
<220> FEATURE:
<223> OTHER INFORMATION: synthetic construct

<400> SEQUENCE: 5

Lys Ile Lys Glu Ile Phe Phe Ile Lys Glu Ile Phe Phe Ile Lys Glu
1               5                   10                  15

Ile Tyr

<210> SEQ ID NO 6
<211> LENGTH: 18
<212> TYPE: PRT
<213> ORGANISM: Artificial Sequence
<220> FEATURE:
<223> OTHER INFORMATION: synthetic construct

<400> SEQUENCE: 6

Lys Val Lys Glu Leu Phe Phe Val Lys Glu Leu Phe Phe Val Lys Glu
1               5                   10                  15

Leu Tyr

<210> SEQ ID NO 7
<211> LENGTH: 18
<212> TYPE: PRT
<213> ORGANISM: Artificial Sequence
<220> FEATURE:
<223> OTHER INFORMATION: synthetic construct

<400> SEQUENCE: 7

Lys Val Lys Glu Ala Phe Phe Val Lys Glu Ala Phe Phe Val Lys Glu
1               5                   10                  15

Ala Tyr

<210> SEQ ID NO 8
<211> LENGTH: 18
<212> TYPE: PRT
<213> ORGANISM: Artificial Sequence
<220> FEATURE:
<223> OTHER INFORMATION: synthetic construct

<400> SEQUENCE: 8

Lys Val Lys Glu Ile Phe Phe Val Lys Glu Ile Phe Phe Val Lys Glu
1               5                   10                  15

Ile Tyr

<210> SEQ ID NO 9
<211> LENGTH: 18
<212> TYPE: PRT
<213> ORGANISM: Artificial Sequence
<220> FEATURE:
<223> OTHER INFORMATION: synthetic construct
```

-continued

```
<400> SEQUENCE: 9

Lys Leu Lys Glu Val Phe Phe Leu Lys Glu Val Phe Phe Leu Lys Glu
1               5                   10                  15

Val Tyr

<210> SEQ ID NO 10
<211> LENGTH: 18
<212> TYPE: PRT
<213> ORGANISM: Artificial Sequence
<220> FEATURE:
<223> OTHER INFORMATION: synthetic construct

<400> SEQUENCE: 10

Lys Leu Lys Glu Ala Phe Phe Leu Lys Glu Ala Phe Phe Leu Lys Glu
1               5                   10                  15

Ala Tyr

<210> SEQ ID NO 11
<211> LENGTH: 18
<212> TYPE: PRT
<213> ORGANISM: Artificial Sequence
<220> FEATURE:
<223> OTHER INFORMATION: synthetic construct

<400> SEQUENCE: 11

Lys Leu Lys Glu Ile Phe Phe Leu Lys Glu Ile Phe Phe Leu Lys Glu
1               5                   10                  15

Ile Tyr

<210> SEQ ID NO 12
<211> LENGTH: 24
<212> TYPE: PRT
<213> ORGANISM: Artificial Sequence
<220> FEATURE:
<223> OTHER INFORMATION: synthetic construct

<400> SEQUENCE: 12

Lys Val Lys Glu Val Phe Phe Val Lys Glu Val Phe Phe Val Lys Glu
1               5                   10                  15

Val Phe Phe Val Lys Glu Val Tyr
            20

<210> SEQ ID NO 13
<211> LENGTH: 30
<212> TYPE: PRT
<213> ORGANISM: Artificial Sequence
<220> FEATURE:
<223> OTHER INFORMATION: synthetic construct

<400> SEQUENCE: 13

Lys Val Lys Glu Val Phe Phe Val Lys Glu Val Phe Phe Val Lys Glu
1               5                   10                  15

Val Phe Phe Val Lys Glu Val Phe Phe Val Lys Glu Val Tyr
            20                  25                  30

<210> SEQ ID NO 14
<211> LENGTH: 36
<212> TYPE: PRT
<213> ORGANISM: Artificial Sequence
<220> FEATURE:
<223> OTHER INFORMATION: synthetic construct

<400> SEQUENCE: 14
```

```
Lys Val Lys Glu Val Phe Phe Val Lys Glu Val Phe Phe Val Lys Glu
1               5                   10                  15

Val Tyr Lys Val Lys Glu Val Phe Phe Val Lys Glu Val Phe Phe Val
            20                  25                  30

Lys Glu Val Tyr
        35

<210> SEQ ID NO 15
<211> LENGTH: 19
<212> TYPE: PRT
<213> ORGANISM: Artificial Sequence
<220> FEATURE:
<223> OTHER INFORMATION: synthetic construct

<400> SEQUENCE: 15

Lys Lys Val Lys Glu Val Phe Phe Val Lys Glu Val Phe Phe Val Lys
1               5                   10                  15

Glu Val Tyr

<210> SEQ ID NO 16
<211> LENGTH: 19
<212> TYPE: PRT
<213> ORGANISM: Artificial Sequence
<220> FEATURE:
<223> OTHER INFORMATION: synthetic construct

<400> SEQUENCE: 16

Lys Val Lys Glu Val Phe Phe Val Lys Glu Val Phe Phe Val Lys Glu
1               5                   10                  15

Val Tyr Lys

<210> SEQ ID NO 17
<211> LENGTH: 60
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<223> OTHER INFORMATION: Xaa may be any naturally-occurring amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
```

```
<222> LOCATION: (23)..(23)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid

<400> SEQUENCE: 17

Lys Xaa Lys Glu Xaa Phe Phe Xaa Lys Glu Xaa Phe Phe Xaa Lys Glu
1               5                   10                  15

Xaa Phe Phe Xaa Lys Glu Xaa Phe Phe Xaa Lys Glu Xaa Phe Phe Xaa
            20                  25                  30

Lys Glu Xaa Phe Phe Xaa Lys Glu Xaa Phe Phe Xaa Lys Glu Xaa Phe
        35                  40                  45

Phe Xaa Lys Glu Xaa Phe Phe Xaa Lys Glu Xaa Tyr
    50                  55                  60

<210> SEQ ID NO 18
<211> LENGTH: 54
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<223> OTHER INFORMATION: Xaa may be any naturally-occurring amino acid
<220> FEATURE:
<221> NAME/KEY: misc_feature
<222> LOCATION: (2)..(2)
<223> OTHER INFORMATION: Xaa can be any naturally occurring amino acid
```

```
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid

<400> SEQUENCE: 18

Lys Xaa Lys Glu Xaa Phe Phe Xaa Lys Glu Xaa Phe Phe Xaa Lys Glu
1               5                   10                  15

Xaa Phe Phe Xaa Lys Glu Xaa Phe Phe Xaa Lys Glu Xaa Phe Phe Xaa
            20                  25                  30

Lys Glu Xaa Phe Phe Xaa Lys Glu Xaa Phe Phe Xaa Lys Glu Xaa Phe
        35                  40                  45
```

Phe Xaa Lys Glu Xaa Tyr
    50

<210> SEQ ID NO 19
<211> LENGTH: 48
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<223> OTHER INFORMATION: Xaa may be any naturally-occurring amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid

<400> SEQUENCE: 19

```
Lys Xaa Lys Glu Xaa Phe Phe Xaa Lys Glu Xaa Phe Phe Xaa Lys Glu
1               5                   10                  15

Xaa Phe Phe Xaa Lys Glu Xaa Phe Phe Xaa Lys Glu Xaa Phe Phe Xaa
            20                  25                  30

Lys Glu Xaa Phe Phe Xaa Lys Glu Xaa Phe Phe Xaa Lys Glu Xaa Tyr
        35                  40                  45
```

<210> SEQ ID NO 20
<211> LENGTH: 42
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<223> OTHER INFORMATION: Xaa may be any naturally-occurring amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid

<400> SEQUENCE: 20

Lys Xaa Lys Glu Xaa Phe Phe Xaa Lys Glu Xaa Phe Phe Xaa Lys Glu
1               5                   10                  15

Xaa Phe Phe Xaa Lys Glu Xaa Phe Phe Xaa Lys Glu Xaa Phe Phe Xaa
            20                  25                  30

Lys Glu Xaa Phe Phe Xaa Lys Glu Xaa Tyr
        35                  40

<210> SEQ ID NO 21
<211> LENGTH: 36
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<223> OTHER INFORMATION: Xaa may be any naturally-occurring amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid

<400> SEQUENCE: 21

Lys Xaa Lys Glu Xaa Phe Phe Xaa Lys Glu Xaa Phe Phe Xaa Lys Glu
1               5                   10                  15

Xaa Phe Phe Xaa Lys Glu Xaa Phe Phe Xaa Lys Glu Xaa Phe Phe Xaa
            20                  25                  30

Lys Glu Xaa Tyr
        35

```
<210> SEQ ID NO 22
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<223> OTHER INFORMATION: Xaa may be any naturally-occurring amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid

<400> SEQUENCE: 22

Lys Xaa Lys Glu Xaa Phe Phe Xaa Lys Glu Xaa Phe Phe Xaa Lys Glu
1               5                   10                  15

Xaa Phe Phe Xaa Lys Glu Xaa Phe Phe Xaa Lys Glu Xaa Tyr
            20                  25                  30

<210> SEQ ID NO 23
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<223> OTHER INFORMATION: Xaa may be any naturally-occurring amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
```

```
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid

<400> SEQUENCE: 23

Lys Xaa Lys Glu Xaa Phe Phe Xaa Lys Glu Xaa Phe Phe Xaa Lys Glu
1               5                   10                  15

Xaa Phe Phe Xaa Lys Glu Xaa Tyr
            20

<210> SEQ ID NO 24
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<223> OTHER INFORMATION: Xaa may be any naturally-occurring amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 24

Lys Xaa Lys Glu Xaa Phe Phe Xaa Lys Glu Xaa Phe Phe Xaa Lys Glu
1               5                   10                  15

Xaa Tyr

<210> SEQ ID NO 25
<211> LENGTH: 12
<212> TYPE: PRT
<213> ORGANISM: Artificial Sequence
```

```
<220> FEATURE:
<223> OTHER INFORMATION: synthetic construct
<220> FEATURE:
<221> NAME/KEY: MISC_FEATURE
<223> OTHER INFORMATION: Xaa may be any naturally-occurring amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 25

Lys Xaa Lys Glu Xaa Phe Phe Xaa Lys Glu Xaa Tyr
1               5                   10

<210> SEQ ID NO 26
<211> LENGTH: 54
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<223> OTHER INFORMATION: Xaa may be any naturally-occurring amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
```

```
<222> LOCATION: (32)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid

<400> SEQUENCE: 26

Lys Xaa Lys Glu Xaa Phe Phe Xaa Lys Glu Xaa Phe Phe Xaa Lys Glu
1               5                   10                  15

Xaa Tyr Lys Xaa Lys Glu Xaa Phe Phe Xaa Lys Glu Xaa Phe Phe Xaa
            20                  25                  30

Lys Glu Xaa Tyr Lys Xaa Lys Glu Xaa Phe Phe Xaa Lys Glu Xaa Phe
        35                  40                  45

Phe Xaa Lys Glu Xaa Tyr
    50

<210> SEQ ID NO 27
<211> LENGTH: 36
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<223> OTHER INFORMATION: Xaa may be any naturally-occurring amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
```

```
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid

<400> SEQUENCE: 27

Lys Xaa Lys Glu Xaa Phe Phe Xaa Lys Glu Xaa Phe Phe Xaa Lys Glu
1               5                   10                  15

Xaa Tyr Lys Xaa Lys Glu Xaa Phe Phe Xaa Lys Glu Xaa Phe Phe Xaa
            20                  25                  30

Lys Glu Xaa Tyr
        35

<210> SEQ ID NO 28
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<223> OTHER INFORMATION: Xaa may be any naturally-occurring amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 28

Lys Xaa Lys Glu Xaa Phe Phe Xaa Lys Glu Xaa Phe Phe Xaa Lys Glu
1               5                   10                  15

Xaa Tyr
```

BIOCOMPATIBLE PROTEIN, BIOCOMPATIBLE PROTEIN GEL AND BIOCOMPATIBLE CONDUCTING PROTEIN GEL COMPRISING THE PROTEIN AND METHOD FOR PREPARING THE SAME

CROSS-REFERENCE TO RELATED APPLICATION

This application claims the benefit of priority under 35 U.S.C. §119(a) of Korean Patent Application No. 10-2014-0095512, filed on Jul. 28, 2014, and Korean Patent Application No. 10-2015-0016171, filed on Feb. 2, 2015 in the Korean Intellectual Property Office, the entire disclosure of each of which is incorporated herein by reference for all purposes.

SEQUENCE LISTING

The instant application contains a Sequence Listing which has been submitted electronically and is hereby incorporated by reference in its entirety.

FIELD

The present invention relates to a biocompatible protein synthesized by protein engineering that does not induce inflammatory responses, a biocompatible protein gel formed using the synthesized protein, and a biocompatible conductive protein gel comprising a protein/nano material complex formed by self-assembling the synthesized protein to a nano material having conductivity.

BACKGROUND

Protein or peptide engineering has recently emerged as a powerful technique as it holds great potential to be used in the fields of biomaterials and biotechnology. Also this technique is expected to have a great market ripple effect as it is applicable to various industrial areas such as development of new medicine, medical engineering and even for national defense industries. Biosynthetic proteins can have advantages over natural proteins in terms of the size, stability, and solubility, and possess a useful functionality that does not exist in human body. Therefore extensive effort has been carried out to develop a self-assembled structure with synthetic peptide or protein, and utilizing nano materials as a scaffold for constructing nano structure with bio soft materials such as DNA, protein, lipids, and amphiphilic peptide is continuously investigated worldwide.

Multifunctional polymer hydrogel is actively studied in various fields such as drug delivery system, bio-sensor, tissue engineering, and micro total analysis system, and its scope of application these days is not just limited in biomedical field, but widening even further. However, most of hydrogel used is based on polymers because hydrogel to be used as a biomaterial is necessary to fulfill critical criteria such as high moisture contents, adjustable viscoelasticity, injectability, and biocompatibility of not causing inflammatory responses when contacting a biological tissue, blood, or body fluid. Hence utilizing protein or peptide as a material for biocompatible hydrogel is being extensively investigated and modification in the peptide or protein sequences is introduced to improve their functionalities of the hydrogel. However, despite of these efforts, current bio soft material based hydrogel is still insufficient to be fully utilized in various area.

So far, types of hydrogel based on natural proteins such as elastin, collagen, gelatin, and globular protein, biosynthetic polypeptide-based hydrogels such as collagen-based synthetic hydrogel, elastin-like polypeptides, silk-elastin-like polypeptide, and coiled-coil motif-based hydrogel, hydrogels using peptides that form beta-pleated-sheets, oligopeptide hydrogels such as amphipathic peptide, multidomain peptide, and hybrid hydrogels combined with polymer are being utilized as biomaterials in development of hydrogels.

However, protein based hydrogel is susceptible to be degraded by proteases residing in living body and therefore increasing biostabiliy and sustainability of such hydrogel is remained as major challenge in developing protein based hydrogel. β-amino acid has been received intensive attention because it is unrecognizable by proteases. There have been a number of reports on a supermolecular hydrogel with self-assembling α-amino acid and β-amino acid with proteolytic stability (Zhimou Yang et al., Small 2007, 3, No. 4, 558-562). A Korean university research team developed a dynamic polypeptide hydrogel which responses to external stimulus and succeeded in forming a self-assembling dynamic polypeptide hydrogel through environment stimulus (Taek Gyoung Kim et al., Ad. Funct. Mater. 2012, 22, 2446-2468).

Furthermore, a recent patent (WO2010/045342) addressed that biostability of a protein is improved by exchanging some α-amino acids of a protein with β-amino acid. In the above patent, about 14% to 50% of α-amino acid residues found in a biologically active polypeptide or fragment are substituted with β-amino acid, and the remained α-amino acid residues were distributed in a repetitive pattern which resulted in improved biostability of the protein.

However, developing a hydrogel with a perfect biostability and biocompatibility is still impeded with critical hindrances, and biocompatible protein gel or biocompatible conductive protein gel that has technical significance in terms of biomaterial has not been developed yet.

SUMMARY

The present disclosure provides a β-amino acid based hydrogel which has biocompatibility that does not provoke inflammatory responses, and proteolytic stability that does not degraded by proteases residing in living body.

Furthermore, by preparing a complex of a synthesized protein and nano materials, the present disclosure may be applied as a conductive biomaterial in various areas such as neurological recovery medicine, drug delivery system and the like.

Furthermore, the present disclosure may be utilized as a biomedical material in regenerative medical areas such as 3D bioprinting.

According to an embodiment of the present disclosure directed to achieve the aforementioned purposes, a biocompatible protein which comprises an amino acid sequence of Lys-X-Lys-Glu-X-Phe-Phe-X-Lys-Glu-X-Phe-Phe-X-Lys-Glu-X-Tyr is synthesized (e.g., SEQ ID NO: 24), where X includes any one or more of hydrophobic amino acids. The amino acid sequence may include any one of SEQ ID NO:2 to SEQ ID NO:11.

The amino acids of the biocompatible protein may be β-amino acids.

Furthermore, the hydrophobic amino acid may include a small size hydrophobic amino acid(s) selected from valine (Val; V), leucine (Leu; L), alanine (Ala; A) and isoleucine (Ile; I).

Furthermore, the amino acid sequence of the biocompatible protein according to the present disclosure may be increased by repetition, and it may include twelve to sixty amino acids. That is, the amino acid sequence may be Lys-X-Lys-(Glu-X-Phe-Phe-X-Lys)$_n$-Glu-X-Tyr, and the sequence may be increased by repetition within a range of n=1 to n=9 (1≤n≤9) (e.g., SEQ ID NO: 17-25). Representatively, the amino acid sequence may be expressed as an amino acid sequence of SEQ ID NO:1, SEQ ID NO:2, SEQ ID NO:12, and SEQ ID NO:13.

Otherwise, the amino acid sequence of the biocompatible protein according to the present disclosure may be (Lys-X-Lys-Glu-X-Phe-Phe-X-Lys-Glu-X-Phe-Phe-X-Lys-Glu-X-Tyr)$_n$, and the sequence may be increased by repetition within a range of n=1 to n=3 (1≤n≤3) (e.g., SEQ ID NO: 26-28). That is, the sequence of each amino acid sequence of SEQ ID NO:2 to SEQ ID NO:11 may be increased by repetition. Representatively, SEQ ID NO:14 is an amino acid sequence that is increased by repetition of SEQ ID NO:2.

Furthermore, lysine (K) may be added to the N-terminus or C-terminus of the amino acid sequence. That is, lysine (K) may be added to the N-terminus or C-terminus of each amino acid sequence of SEQ ID NO:1 to SEQ ID NO:14. Representatively, SEQ ID NO:15 and SEQ ID NO:16 are amino acid sequences where lysine is added to the N-terminus and C-terminus of SEQ ID NO:2, respectively.

Furthermore, the biocompatible protein of the present disclosure may not be degraded by an enzyme. The enzyme may be a protease that includes one or more of trypsin, chymotrypsin, and subtilisin.

The biocompatible protein of the present disclosure may include all β-amino acid sequences in which a repetitive pattern of three (3) amino acid sequences, that is, a small size hydrophobic β-amino acid residing in the middle, and two β-amino acids having a positive charge, negative charge, or hydrophobic property positioning in the front and back, respectively, is distributed. Therefore, the amino acid sequences of SEQ ID NO:1 to SEQ ID NO:16 may be modified according to the repetitive pattern.

Furthermore, a biocompatible protein gel of the present disclosure may include a biocompatible protein according to the present disclosure. Herein, an amino acid sequence including a β-amino acid may include Lys-X-Lys-Glu-X-Phe-Phe-X-Lys-Glu-X-Phe-Phe-X-Lys-Glu-X-Tyr (e.g., SEQ ID NO: 24) or Lys-X-Lys-(Glu-X-Phe-Phe-X-Lys)$_n$-Glu-X-Tyr (1≤n≤9) (e.g., SEQ ID NO: 17-25), wherein X includes any one or more of hydrophobic amino acids. The biocompatible protein being used may include any one or more of amino acid sequences expressed as SEQ ID NO:1 to SEQ ID NO:16.

Furthermore, the biocompatible conductive protein gel of the present disclosure may include a complex of a biocompatible protein and a conductive nano material. Herein, the biocompatible protein comprises an amino acid sequence including β-amino acids, which represented as Lys-X-Lys-Glu-X-Phe-Phe-X-Lys-Glu-X-Phe-Phe-X-Lys-Glu-X-Tyr (e.g., SEQ ID NO: 24) or Lys-X-Lys-(Glu-X-Phe-Phe-X-Lys)$_n$-Glu-X-Tyr (n=1 to n=9, 1≤n≤9) (e.g., SEQ ID NO: 17-25), wherein X may include any one or more of hydrophobic amino acids. The biocompatible protein may include any one or more of amino acid sequences expressed as SEQ ID NO:1 to SEQ ID NO:16.

Furthermore, the biocompatible conductive protein gel may include any one or more of a carbon nanotube (CNT), fullerene ($C_{60}$), conductive polymer nanowire, conductive polymer nanotube, conductive polymer nanoparticle, metal nanowire, and metal nanoparticle. The carbon nanotube may be a single-walled carbon nanotube or multi-walled carbon nanotube.

According to another embodiment of the present disclosure, there is provided a method for preparing a biocompatible protein, the method comprising: coupling a β-amino acid to a solid-phase resin (S10); synthesizing a β-peptide by removing a Fmoc (fluorenyl methyl oxycarbonyl) protecting group from the β-amino acid and connecting a next β-amino acid to the β-amino acid (S11); and separating the β-peptide from the solid-phase resin (S12). Herein, the β-peptide may include an amino acid sequence of Lys-X-Lys-Glu-X-Phe-Phe-X-Lys-Glu-X-Phe-Phe-X-Lys-Glu-X-Tyr (e.g., SEQ ID NO: 24) or Lys-X-Lys-(Glu-X-Phe-Phe-X-Lys)$_n$-Glu-X-Tyr (1≤n≤9) (e.g., SEQ ID NO: 17-25), wherein X includes any one or more of hydrophobic amino acids. The amino acid sequence may include any one or more of amino acid sequences of SEQ ID NO:1 to SEQ ID NO:16.

According to another embodiment of the present disclosure, there is provided a method for preparing a biocompatible protein gel, the method comprising: dissolving a biocompatible protein consisting of β-amino acids in a buffer solution to make the biocompatible protein into a gel. The biocompatible protein consisting of β-amino acids may include an amino acid sequence of Lys-X-Lys-Glu-X-Phe-Phe-X-Lys-Glu-X-Phe-Phe-X-Lys-Glu-X-Tyr (e.g., SEQ ID NO: 24) or Lys-X-Lys-(Glu-X-Phe-Phe-X-Lys)$_n$-Glu-X-Tyr (1≤n≤9) (e.g., SEQ ID NO: 17-25), wherein X includes any one or more of hydrophobic amino acids. The amino acid sequence may include any one or more of SEQ ID NO:1 to SEQ ID NO:16.

According to another embodiment of the present disclosure, there is provided a method for preparing a biocompatible conductive protein gel, the method comprising: preparing a protein solution by dissolving a biocompatible protein consisting of β-amino acids in a buffer solution (S20); preparing an aqueous solution of a conductive nano material by dispersing a conductive nano material in a glycerol aqueous solution (S21); forming a biocompatible protein/nano material complex by mixing the protein solution and the conductive nano material aqueous solution (S22); concentrating the protein/nano material complex (S23); and making the protein/nano material complex into a gel by adding a biocompatible protein that has started to be fibrosized to the concentrated protein/nano material complex (S24).

The biocompatible protein may include an amino acid sequence of Lys-X-Lys-Glu-X-Phe-Phe-X-Lys-Glu-X-Phe-Phe-X-Lys-Glu-X-Tyr (e.g., SEQ ID NO: 24) or Lys-X-Lys-(Glu-X-Phe-Phe-X-Lys)$_n$-Glu-X-Tyr (1≤n≤9) (e.g., SEQ ID NO: 17-25), wherein X includes any one or more of hydrophobic amino acids. The amino acid sequence may include any one or more of SEQ ID NO:1 to SEQ ID NO:16.

The biocompatible conductive protein gel may include any one or more of a carbon nanotube (CNT), fullerene ($C_{60}$), conductive polymer nanowire, conductive polymer nanotube, conductive polymer nanoparticle, metal nanowire, and metal nanoparticle. Furthermore, the carbon nanotube may be a single-walled carbon nanotube or multi-walled carbon nanotube.

Furthermore, the step of forming a biocompatible protein/nano material complex may include self-assembling the protein to the nano material. The step of forming a biocompatible protein/nano material complex may include mixing the protein solution and the conductive nano material aqueous solution in a volume ratio of 1:1 to 10:1.

A biocompatible protein, and a biocompatible protein gel and a biocompatible conductive protein gel comprising the same according to the various aforementioned embodiments of the present disclosure are prepared by synthesizing a protein from unnatural biological β-amino acids, and thus are advantageous since they causes no rejections from a human body and are not easily degradable, thereby exhibiting biostability.

Furthermore, a complex of the synthesized biocompatible protein according to the present disclosure and a nano material may be used as a conductive biomaterial for neurological recovery medicine and drug delivery system where biostability and bioconductivity are remained as challenging thresholds.

Moreover, the present disclosure may be utilized as a biomedical material for regenerative medicine such as 3D bio-printing.

DETAILED DESCRIPTION

Figure 1:
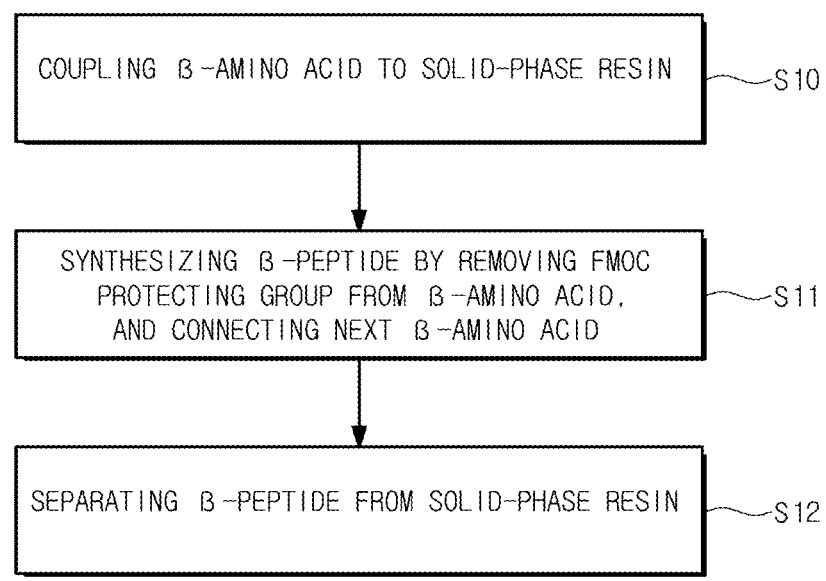
FIG. 1 shows a flowchart of a method for preparing a biocompatible protein according to the present disclosure.

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

Furthermore, a singular form may include a plural form as long as it is not specifically mentioned in a sentence. Furthermore, "include/comprise" or "including/comprising" used in the specification represents that one or more components, steps, operations, and elements exist or are added.

Furthermore, unless defined otherwise, all the terms used in this specification including technical and scientific terms have the same meanings as would be generally understood by those skilled in the related art. The terms defined in generally used dictionaries should be construed as having the same meanings as would be construed in the context of the related art, and unless clearly defined otherwise in this specification, should not be construed as having idealistic or overly formal meanings.

The present disclosure relates to a biocompatible protein that is synthesized by protein engineering and that causes no rejection from human bodies, a biocompatible protein gel formed using the synthesized protein, and a biocompatible conductive protein gel comprising a protein/nano material complex formed by self-assembling the synthesized protein to a nano material having conductivity.

A biocompatible protein according to the present disclosure comprises a β-peptide characterized by a helical structure, which includes an amino acid sequence having a repetitive pattern of three (3) β-amino acids. The three β-amino acids includes a small size hydrophobic β-amino acid selected from valine (Val, V), leucine (Leu, L), alanine (Ala, A) and isoleucine (Ile, I) in the middle, and two amino acid residues having positive charges, negative charges, or hydrophobic properties in the front and back, respectively.

The aforementioned amino acid sequence has been predicted and designed as such a β-peptide helical structure based on the diversity of protein frames, parameterization of secondary structures, rotamer libraries of side branches, and energy optimization calculation, using the molecular dynamics simulation method.

In an embodiment, the amino acid sequence of the biocompatible protein according to the present disclosure is Lys-X-Lys-Glu-X-Phe-Phe-X-Lys-Glu-X-Phe-Phe-X-Lys-Glu-X-Tyr (e.g., SEQ ID NO: 24), wherein X may include any one or more of hydrophobic amino acids. The amino acid sequence may include any one of amino acid SEQ ID NO:2 to SEQ ID NO:11 shown below.

```
                                        (SEQ ID NO: 2)
Ac-KVK EVF FVK EVF FVK EVY-NH2

(SEQ ID NO: 3)
Ac-KLK ELF FLK ELF FLK ELY-NH2

(SEQ ID NO: 4)
Ac-KAK EAF FAK EAF FAK EAY-NH2

(SEQ ID NO: 5)
Ac-KIK EIF FIK EIF FIK EIY-NH2

(SEQ ID NO: 6)
Ac-KVK ELF FVK ELF FVK ELY-NH2

(SEQ ID NO: 7)
Ac-KVK EAF FVK EAF FVK EAY-NH2

(SEQ ID NO: 8)
Ac-KVK EIF FVK EIF FVK EIY-NH2
```

-continued

```
                                               (SEQ ID NO: 9)
Ac-KLK EVF FLK EVF FLK EVY-NH2

(SEQ ID NO: 10)
Ac-KLK EAF FLK EAF FLK EAY-NH2

(SEQ ID NO: 11)
Ac-KLK EIF FLK EIF FLK EIY-NH2
```

The amino acid of the biocompatible protein according to the present disclosure is characterized as being consisted of β-amino acids with no degradability inside a human body.

Furthermore, the hydrophobic amino acid is characterized as being a small size hydrophobic amino acid selected from valine (Val, V), leucine (Leu, L), alanine (Ala, A) and isoleucin (Ile, I).

Moreover, the amino acid sequence of the biocompatible protein according to the present disclosure may be increased by repetition, and it may include twelve to sixty amino acids. That is, the amino acid sequence may be Lys-X-Lys-(Glu-X-Phe-Phe-X-Lys)$_n$-Glu-X Tyr, and the sequence may be increased by repetition within a range of n=1 to n=9 (1≤n≤9) (e.g., SEQ ID NO: 17-25). Representatively, the amino acid sequences may be expressed as SEQ ID NO:1, SEQ ID NO:2, SEQ ID NO:12 and SEQ ID NO:13.

```
                                               (SEQ ID NO: 1)
Ac-KVK EVF FVK EVY-NH2

(SEQ ID NO: 2)
Ac-KVK EVF FVK EVF FVK EVY-NH2

(SEQ ID NO: 12)
Ac-KVK EVF FVK EVF FVK EVF FVK EVY-NH2

(SEQ ID NO: 13)
Ac-KVK EVF FVK EVF FVK EVF FVK EVF FVK EVY-NH2
```

Otherwise, the amino acid sequence of the biocompatible protein according to the present disclosure may be (Lys-X-Lys-Glu-X-Phe-Phe-X-Lys-Glu-X-Phe-Phe-X-Lys-Glu-X-Tyr)$_n$, and it may be increased by repetition within a range of n=1 to n=3 (1≤n≤3) (e.g., SEQ ID NO: 26-28). That is, the sequence of each of SEQ ID NO:2 to SEQ ID NO:11 may be increased by repetition. Representatively, SEQ ID NO:14 is an amino acid sequence that is increased by repetition of SEQ ID NO:2.

```
                                               (SEQ ID NO: 14)
Ac-KVK EVF FVK EVF FVK EVY KVK EVF FVK EVF FVK

EVY-NH2
```

Furthermore, an amino acid sequence of the biocompatible protein according to the present disclosure may include a lysine (K) being added to an N-terminus or C-terminus. That is, in each amino acid sequence of SEQ ID NO:1 to SEQ ID NO:14, lysine (K) may be added to the N-terminus or C-terminus. Representatively, SEQ ID NO:15 and SEQ ID NO:16 are amino acid sequences wherein lysine(K) is added to the N-terminus and C-terminus of SEQ ID NO:2, respectively.

```
                                               (SEQ ID NO: 15)
Ac-K KVK EVF FVK EVF FVK EVY-NH2

(SEQ ID NO: 16)
Ac-KVK EVF FVK EVF FVK EVY K-NH2
```

SEQ ID NO:1 to SEQ ID NO:16 are characterized as β-peptides consisting of β-amino acids having no degradability in a human body.

Furthermore, the biocompatible protein of the present disclosure may not be degraded by an enzyme. The enzyme may desirably include a protease. More desirably, the enzyme may be a protease that includes any one or more of trypsin, chymotrypsin, and subtilisin.

Furthermore, the biocompatible protein according to the present disclosure may include all β-amino acid sequences in which a repetitive pattern of three (3) amino acid sequences, that is, a small size hydrophobic β-amino acid residing in the middle, and two β-amino acids having a positive charge, negative charge, or hydrophobic property positioning in the front and back, respectively, is distributed. Desirably, the amino acid sequences of SEQ ID NO:1 to SEQ ID NO:16 are modifiable according to the repetitive pattern.

Furthermore, a biocompatible protein gel of the present disclosure may be prepared by using a biocompatible protein. Desirably, the biocompatible protein gel may include an amino sequence consisting of β-amino acids, which may be Lys-X-Lys-Glu-X-Phe-Phe-X-Lys-Glu-X-Phe-Phe-X-Lys-Glu-X-Tyr (e.g., SEQ ID NO: 24) or Lys-X-Lys-(Glu-X-Phe-Phe-X-Lys)$_n$-Glu-X-Tyr (n=1 to n=9, 1≤n≤9) (e.g., SEQ ID NO: 17-25), wherein X may include any one or more of hydrophobic amino acids. The biocompatible protein may include any one or more of amino acid sequences expressed as SEQ ID NO:1 to SEQ ID NO:16.

Furthermore, the present disclosure may provide a biocompatible conductive protein gel including a complex of a biocompatible protein and a conductive nano material.

Desirably, in the biocompatible conductive protein gel may comprise an amino acid sequence consisting of β-amino acids of Lys-X-Lys-Glu-X-Phe-Phe-X-Lys-Glu-X-Phe-Phe-X-Lys-Glu-X-Tyr (e.g., SEQ ID NO: 24) or Lys-X-Lys-(Glu-X-Phe-Phe-X-Lys)$_n$-Glu-X-Tyr (n=1 to n=9, 1≤n≤9) (e.g., SEQ ID NO: 17-25), wherein X may include any one or more of hydrophobic amino acids. The biocompatible protein may comprise any one or more of the amino acid sequences expressed as SEQ ID NO:1 to SEQ ID NO:16.

Furthermore, the conductive nano material may include any one or more of a carbon nanotube (CNT), fullerene ($C_{60}$), conductive polymer nanowire, conductive polymer nanotube, conductive polymer nanoparticle, metal nanowire, and metal nanoparticle.

Desirably, the conductive nano material may include a carbon nanotube having a large surface area, and high elastic modulus, tensile strength and electrical conductivity, thereby being applicable in various ways.

More desirably, the conductive nano material may be a single-walled carbon nanotube or multi-walled carbon nanotube that may have excellent conductivity even when combined with a protein gel having excellent biocompatibility in a human body so as to form a complex.

Furthermore, a method for preparing a biocompatible protein according to the present disclosure may comprise a step of coupling a β-amino acid to a solid-phase resin (S10); a step of synthesizing a β-peptide by removing a Fmoc (fluorenyl methyl oxycarbonyl) protecting group from the β-amino acid, and a step of connecting a next β-amino acid to the β-amino acid (S11); and a step of separating the β-peptide from the solid-phase resin (S120) (See FIG. 1). Desirably, in the β-peptide, an amino acid sequence may include Lys-X-Lys-Glu-X-Phe-Phe-X-Lys-Glu-X-Phe-Phe-X-Lys-Glu-X-Tyr (e.g., SEQ ID NO: 24) or Lys-X-Lys- (Glu-X-Phe-Phe-X-Lys)$_n$-Glu-X-Tyr (n=1 to n=9, 1≤n≤9) (e.g., SEQ ID NO: 17-25), wherein X may include any one or more of hydrophobic amino acids. The amino acid sequence may include any one or more of SEQ ID NO:1 to SEQ ID NO:16.

Furthermore, a method for preparing a biocompatible protein gel of the present disclosure may comprise a step of making a biocompatible protein into a gel by dissolving the biocompatible protein consisting of β-amino acids in a buffer solution. Desirably, in the method for preparing a biocompatible protein gel, the biocompatible protein may include an amino acid sequence of Lys-X-Lys-Glu-X-Phe-Phe-X-Lys-Glu-X-Phe-Phe-X-Lys-Glu-X-Tyr (e.g., SEQ ID NO: 24) or Lys-X-Lys-Glu-X-Phe-Phe-X-Lys)$_n$-Glu-X-Tyr (n=1 to n=9, 1≤n≤9) (e.g., SEQ ID NO: 17-25), wherein X may include any one or more of hydrophobic amino acids. The biocompatible protein may include amino acid sequence(s) of any one or more of SEQ ID NO:1 to SEQ ID NO:16.

Figure 2:
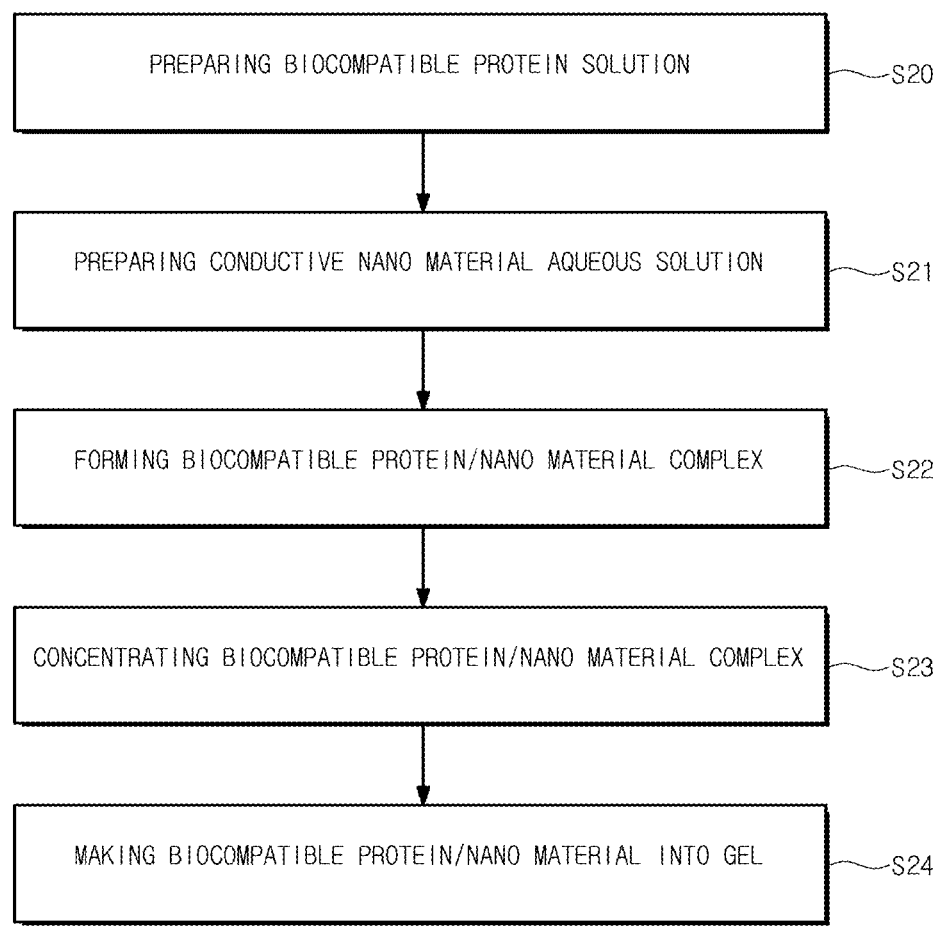
FIG. 2 shows a flowchart of a method for preparing a biocompatible conductive protein gel according to the present disclosure.

Furthermore, the method for preparing a biocompatible conductive protein gel of the present disclosure may include a step of preparing a biocompatible protein solution by dissolving a biocompatible protein consisting of β-amino acids in a buffer solution (S20); a step of preparing a conductive nano material aqueous solution by dispersing a conductive nano material in a glycerol aqueous solution (S21); a step of forming a biocompatible protein/nano material complex by mixing the protein solution and the nano material aqueous material (S22); a step of concentrating the protein/nano material complex (S23); and a step of making the biocompatible protein into a gel by adding a biocompatible protein that has started being fibrosized to the concentrated protein/nano material complex (S24) (See FIG. 2).

The biocompatible conductive protein gel may include an amino acid sequence of Lys-X-Lys-Glu-X-Phe-Phe-X-Lys-Glu-X-Phe-Phe-X-Lys-Glu-X-Tyr (e.g., SEQ ID NO: 24) or Lys-X-Lys-Glu-X-Phe-Phe-X-Lys)$_n$-Glu-X-Tyr (n=1 to n=9, 1≤n≤9) (e.g., SEQ ID NO: 17-25), wherein X may include any one or more of hydrophobic amino acids. The biocompatible protein may include amino acid sequence(s) of any one or more of SEQ ID NO:1 to SEQ ID NO:16.

Furthermore, the biocompatible conductive protein gel may include any one or more of conductive nano materials of carbon nanotube (CNT), fullerene (C$_{60}$), conductive polymer nanowire, conductive polymer nanotube, conductive polymer nanoparticle, metal nanowire, and metal nanoparticle. Desirably, the biocompatible conductive protein gel may include a carbon nanotube as conductive nano material. More desirably, the biocompatible conductive protein gel may include a single-walled carbon nanotube or multi-walled carbon nanotube as conductive nanomaterial.

Furthermore, the step of forming a biocompatible protein/nano material complex may include self-assembling the protein to the nano material. The step of forming a biocompatible protein/nano material complex may include mixing the biocompatible protein solution and the conductive nano material aqueous solution in a volume ratio of 1:1 to 10:1. Desirably, the protein concentration must be 1 mg/mL or above.

The present disclosure includes a protein gel that has excellent biocompatibility and that is self-assembled, and thus does not provoke an inflammation responses from human body which is considered as a major problems with current materials used in medical areas, and may thus be used in coating medical means such as implants and artificial internal organs. Furthermore, the present disclosure includes a conductive biomaterial capable of resolving the problems of biodegradability and bioconductivity, and is thus expected to have a significant impact on various application fields of medical industries such as neurological recovery medicine, drug delivery system, conductive flexible coating, tissue engineering, and optogenetics and the like. Furthermore, along with the recent development of 3D printing technique and a conductive flexible material in bioprinting studies aimed at overcoming the biocompatibility problem in medical material, the present disclosure is expected to provide materials applicable as a source material for customized internal organs, artificial muscles, and artificial skin and the like.

Hereinafter, the present disclosure will be explained in further detail based on the examples below, but the examples are for illustrative purpose only, not to limit the scope of the claims attached hereto.

EXAMPLES

Figure 3:
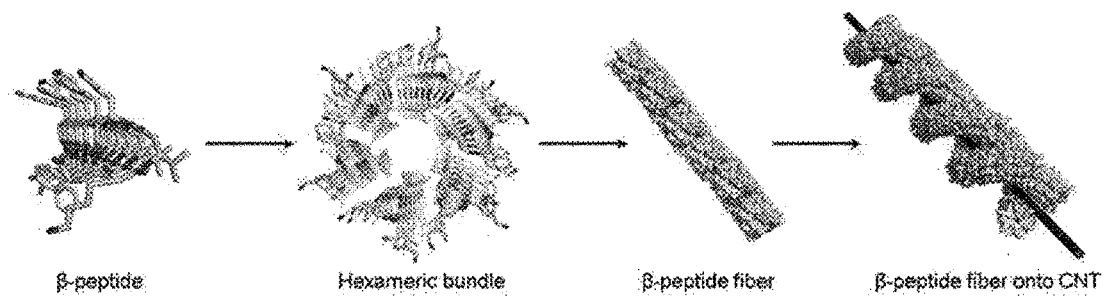
FIG. 3 shows a mimetic diagram illustrating a complex of a biocompatible β-peptide and carbon nanotube through molecular dynamic simulation.

FIG. 3 is a mimetic diagram illustrating a complex of a biocompatible β-peptide and carbon nanotube through protein computer simulation;

In the examples below, β-peptide (β-VhexS) of SEQ ID NO:2 consisting of eighteen β-amino acids is exemplified.

Example 1: Preparing Biocompatible β-Peptide

β-peptide was synthesized by a microwave synthesizer made by CEM Corporation (Discover SPS, 200-240V/50/60 Hz). β-amino acid having C-terminal activated with HBTU (2-(1H-Benzotriazole-1-yl)-1,1,3,3-tetramethyl uronium hexafluorophosphate) was synthesized using an inactivated solid-phase H-rink amide resin (PCAS 0.53 mmol substitution) by the Fmoc (fluorenylmethyloxycarbonyl carbamate) method as a solid-phase peptide synthesizing method.

First of all, the resin was inflated in N,N-dimethyl formamide (hereinafter referred to as DMF) for 30 minutes, and then deprotected three times for two minutes at 80° C. using 20% piperidine (DMF solution). The coupling ratio of amino acid:HBTU:DIEA (N,N-Diisopropyl ethylamine):resin was 3:2.5:4:1. β-amino acid, HBTU and DIEA were mixed well, and the reaction in the resin was proceeded a total of three times for two minutes at 70° C.

After each deprotecting and coupling step, washing process was proceeded using DMF and dichloromethane (hereinafter referred to as DCM) three times each. After six residues were synthesized from C-terminus, the deprotecting and coupling time were extended to four minutes, and after twelve residues were synthesized, the deprotecting and coupling time were extended to eight minutes, and the deprotecting reaction was also increased to five times. After all the β-amino acid residues were synthesized, the Fmoc protecting group of the amino acid at N-terminus was removed by the same deprotecting reaction as in the former step. Lastly, any specimen left was removed using ethanol, and then dried under a vacuum state. To separate β-peptide from the solid-phase resin, the synthesized resin was reacted for two hours in a cleavage solution containing 95:2.5:2.5 of TFA (Trifluoroacetic acid):TIS(Triisopropyl silane):distilled water in volume ratio and then the resin was filtered by an asbestos filter. The cleavage solution in the filtered solution was vaporized under nitrogen gas, and it was precipitated by diethyl ether that had been kept under cold temperature. Herein, the precipitated matter was β-peptide. The β-peptide, the precipitated matter was then dried under a vacuum state, and then dissolved by distilled water and acetonitrile (hereinafter referred to as ACN) and then freeze-dried.

From the freeze-dried β-peptide, a biocompatible protein β-VhexS having a mass of 2516 was confirmed through Maldi-Tof mass analysis.

The β-peptide synthesized by the solid-phase peptide method needs to be refined using high performance liquid chromatography in order to increase the purity, and thus the β-peptide was refined using Waters Prep 150 LC system and XBridge BEH300 Prep C4 5 µm column.

Figure 4:
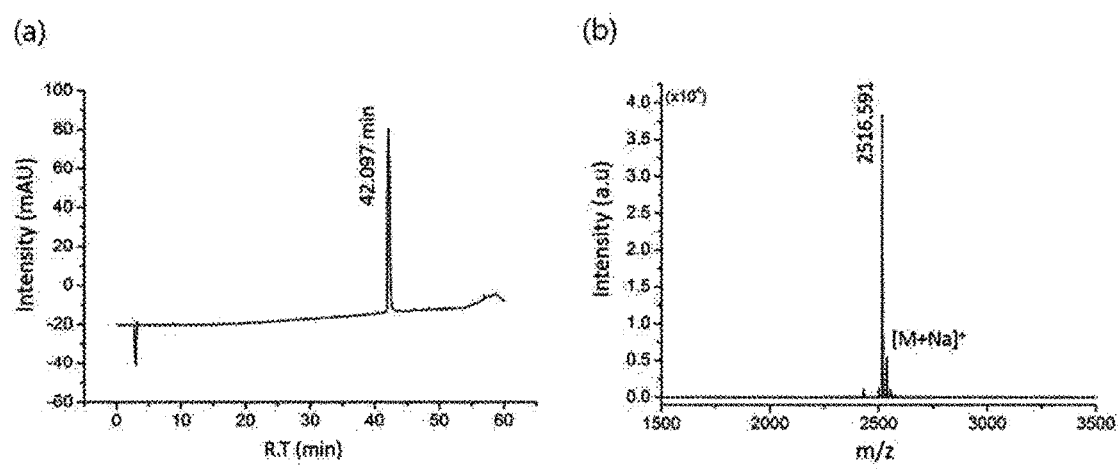
FIG. 4 shows results of analyzing the β-peptide through HPLC (a) MALDI-TOF (b).

The refined β-peptide was analyzed by Agilent ZORBAX 300SB-C3 using an analyzing Agilent 1260 HPLC, and it was confirmed that the purity was 90% or above (FIG. 4a), and through Maldi-Tof mass analysis, it was confirmed that the refined β-peptide was the biocompatible protein β-VhexS of the present disclosure (FIG. 4b).

TEM (Transmission Electron Microscope) Analysis

Figure 5:
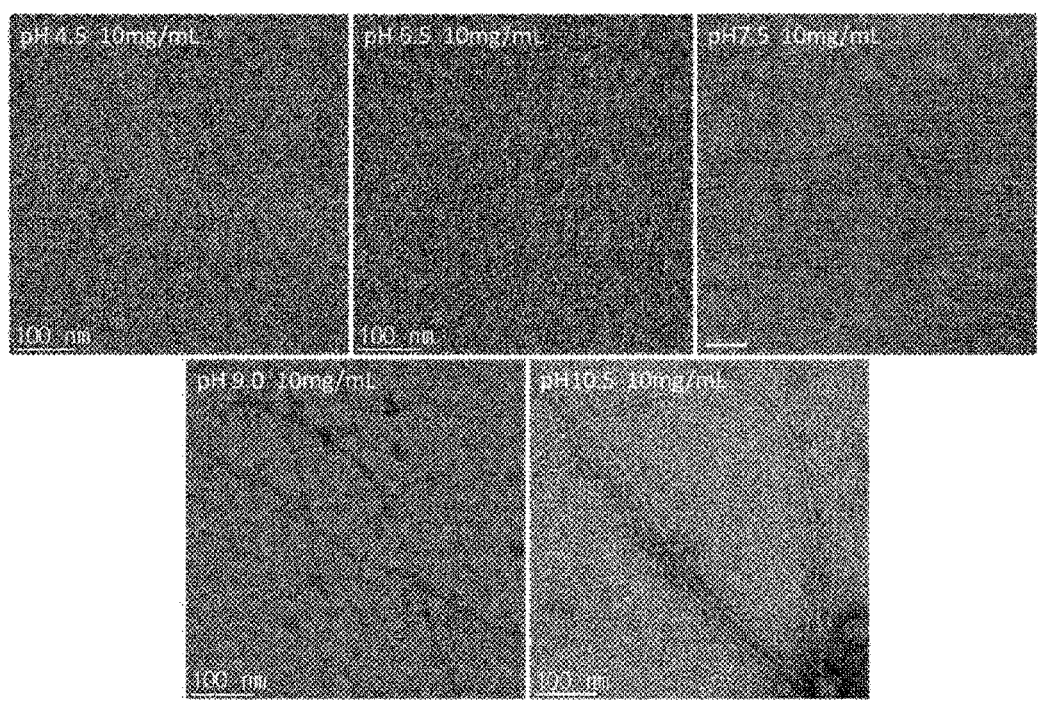
FIG. 5 shows TEM images of biocompatible protein gels with different pH.
Figure 6:
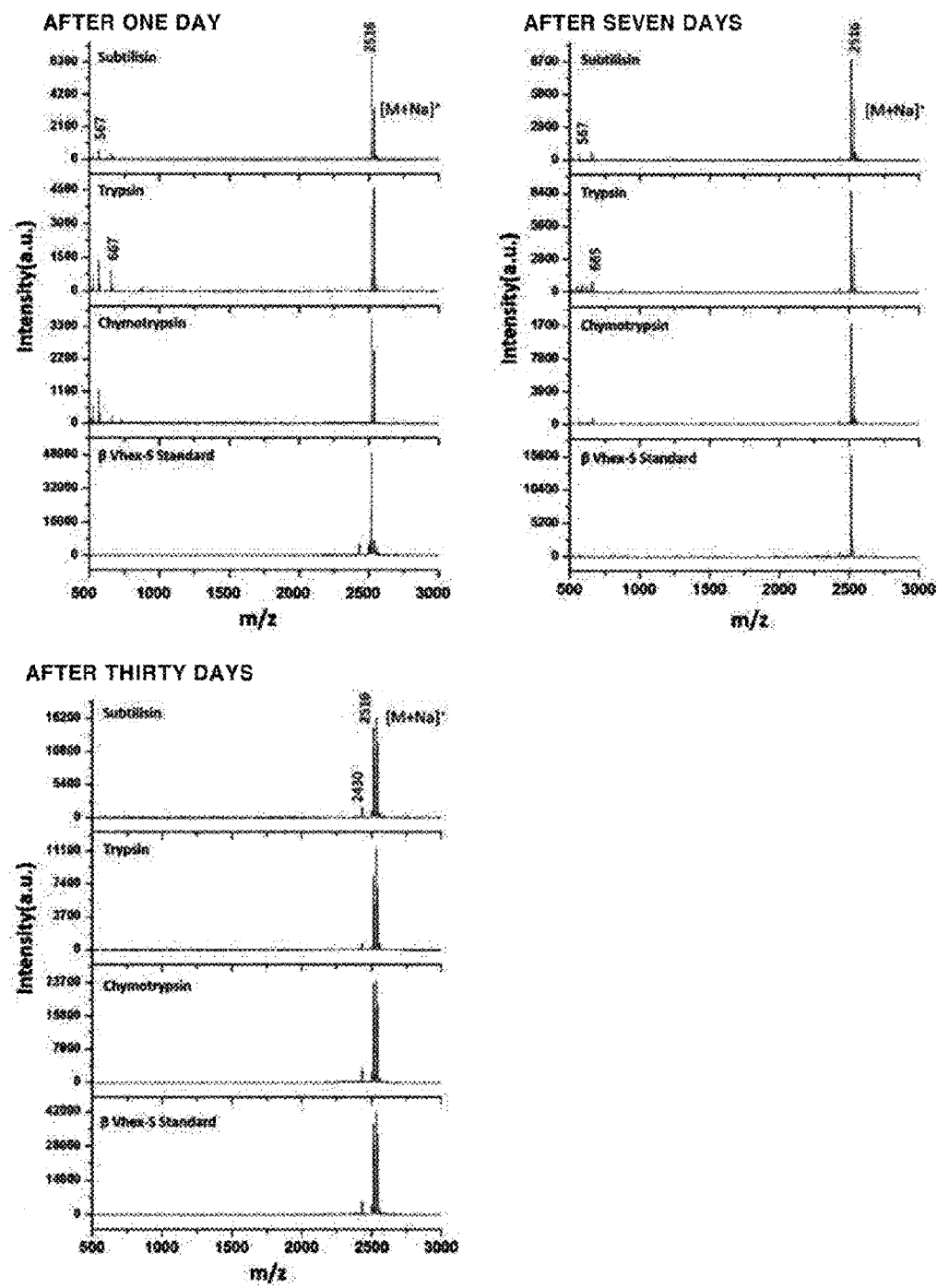
FIG. 6 shows results of analyzing degradation of the β-peptide by a protease through MALDI-TOF.

FIG. 5 shows results of measurements using high resolution TEM (HRTEM; JEM-2100F). That is, 100 mg of uranyl acetate was dissolved in 5 mL of boiled distilled water to make 20 mg/mL of uranyl acetate solution, and then mixed for 5 minutes using a magnetic stirrer. Then, the solution was filtered using a 0.22 µm syringe filter, and then 500 µL of uranyl acetate solution and 12.5 µL of 200 mM NaOH aqueous solution were added into a micro tube. The β-peptide solution to be analyzed was placed on a Formvar/carbon TEM grid, and before being completely dried, the uranyl acetate solution was dropped to dye the solution. According to measurement results, β-peptide showed different aspects of fibrolization depending on pH conditions, and it was confirmed that under an alkaline condition (pH 9.0), two β-peptide strands were twisted once more, thereby forming thicker fiber.

Analysis on Whether or Not β-Peptide is Degraded by Protease

In order to confirm whether β-peptide is degraded by a protease, proteolytic susceptibility of β-VhexS was measured with trypsin, chymotrypsin, and subtilisin which cleave protein nonspecifically. Peptide and pretease stock solution was prepared by desolving 100 µM of beta-VhexS and 200 µM of each pretease in TBS buffer at pH 7.5. 10 µL of stock solution. 40 µL of peptide stock solution and 10 µL of protease stock solution were transferred into micro tube and incubated for one, seven, thirty days at room temperature. The reaction was quenched with adding 100 µL of 1% TFA solution. As a control sample, 40 µL of peptide stock solution without protease was also treated with 1% TFA solution.

Degree of peptide degradation was analyzed with high performance liquid chromatography using C3 column for Agilent analysis. Analysis results showed that there was no difference between the peptide standard sample and specimens that had been processed with the protease, and thus it is confirmed that unlike α-amino acid, β-amino acid is not degraded by the protease. The HPLC peaks of both standard sample and enzyme treated peptide sample were compared, and the peaks appeared only for enzyme treated sample were analyzed with MALDI-TOF. The results confirmed that β-peptide was not degraded by enzymes.

Example 2: Preparing Biocompatible β-Peptide Gel

Figure 7:
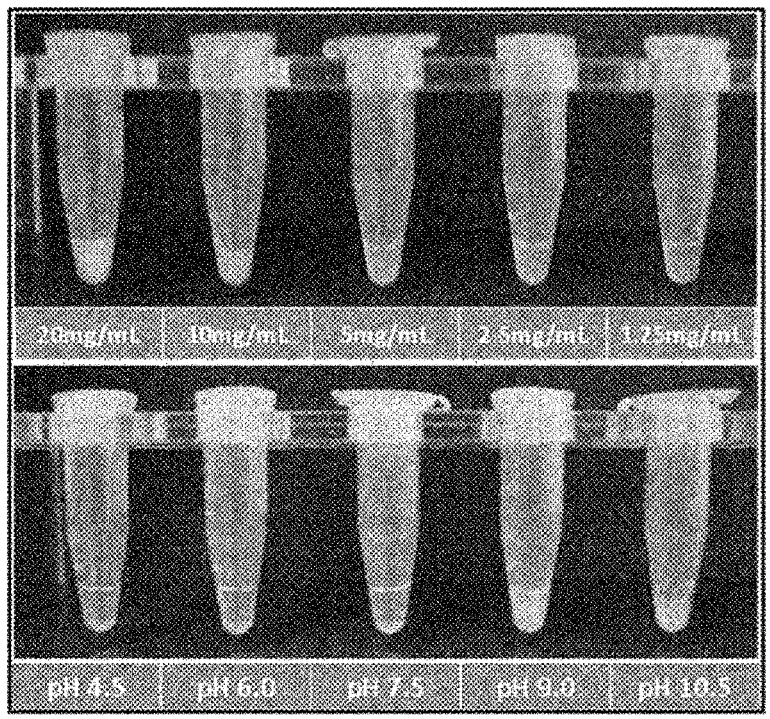
FIG. 7 shows images of biocompatible protein gels with different protein concentrations and pH.
Figure 8:
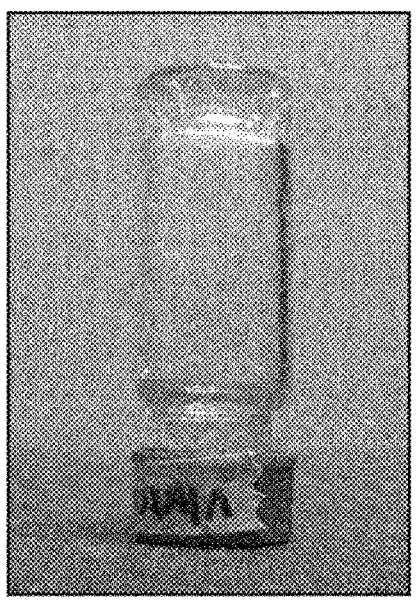
FIG. 8 shows a photograph of a biocompatible protein gel prepared according to the present disclosure.

In order to prepare a physical gel of β-peptide, a freeze-dried β-peptide was kept at room temperature for about 30 minutes to adjust the temperature of the β-peptide to room temperature (15° C. to 25° C.). The protein was then dissolved in a buffer solution and ultrapure water while changing a concentration and pH condition, and incubated in room temperature for about three hours to prepare β-peptide gel. In order to prepare β-peptide gels of different physical characteristics, protein gels were prepared each having different concentration of peptide (1.25, 2.5, 5, 10, 20, 30, 50 mg/mL), and in order to prepare protein gels of different chemical characteristics, protein gels were prepared each with a different pH of solvent used for dissolving the protein (pH 4.5, 6.0, 7.5, 9.0, 10.5) (FIG. 7). As a result, it was confirmed that properties of a protein gel can be modified by adjusting the concentration of the protein. FIG. 8 is a photograph of the protein gel prepared to have a protein concentration of 50 mg/mL.

Example 3: Preparing β-Peptide/SWNT Complex

In a 50 mL falcon tube, 20 mg of single-walled carbon nanotube (hereinafter referred to as SWNT) was placed, and then dissolved in 20 mL of 1 wt % glycerol aqueous solution. For SWNT dispersion, a tip of a sonicator (max power 125 W) was placed at a ⅓ of the prepared solution from bottom, and ultrasound waves were applied for twenty minutes at 2/1 second(s) on/off at 40% power. Herein, the falcon tube containing the solution was sufficiently plunged in ice. As a result of applying the ultrasound waves, the SWNT glycerol solution showed a uniform black color. 3 mL of the solution was then put into a 15 mL falcon tube, and centrifuged at 7,000 rpm for 10 minutes, which made the SWNT precipitate.

The supernatant fluid was entirely removed using a Pasteur pipette, and then 3 mL of distilled water was added to resuspend the same. When the SWNT did not disperse well, ultrasound waves were applied again. The re-dispersed solution was centrifuged, and then this process was repeated twice.

Figure 9:
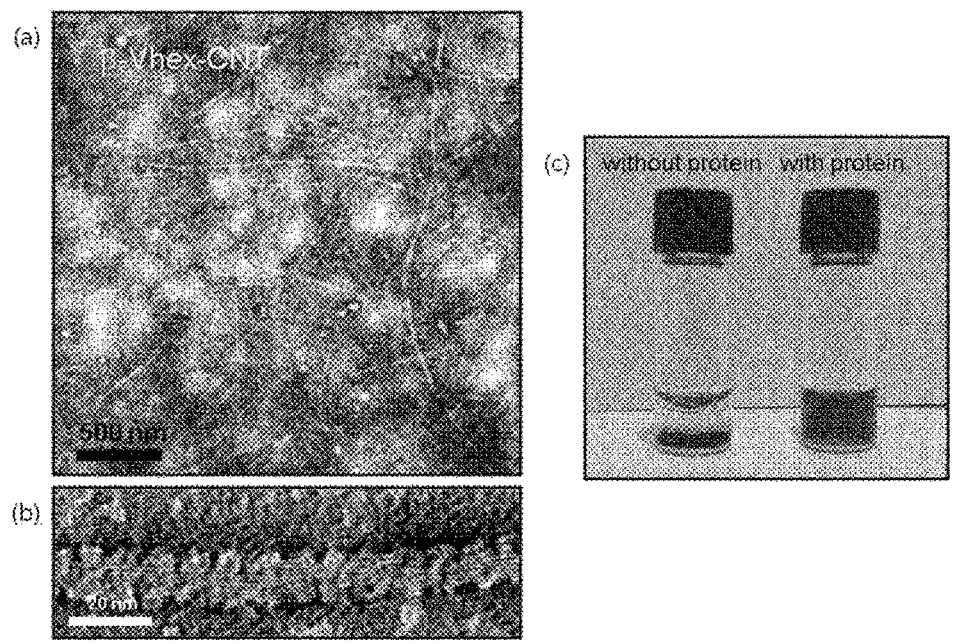
FIG. 9 shows TEM images for showing the degree of dispersion of carbon nanotube before and after applying ultrasonic waves in order to form a β-peptide/carbon nanotube complex (low magnification (a), high magnification (b), image for comparison after applying ultrasonic waves with and without peptide (c)).

5.5 mg of β-peptide was taken and dissolved in a 5 mL of a buffer solution containing 20 nM Tris and 100 mM NaCl, and then the peptide solution was transferred to the falcon tube having the SWNT from which glycerol had been removed. The falcon tube containing this solution was sufficiently plunged in ice, and then ultrasound waves were applied for 30 minutes at 2/1 second(s) on/off condition at 60% power. The SWNT wrapped with β-peptide was able to well dispersed in the buffer and a black colored solution was obtained as a result. The β-peptide/SWNT complex of the present disclosure was obtained after the mixture from the previous step was centrifuged for 10 min at 7,000 rpm to selectively obtain the SWNT dispersed by self-assembling of β-peptide. FIG. 9 shows photographs for comparison of the degree of dispersion of the SWNT of before and after applying the ultrasound waves, and a TEM analysis photograph.

Circular Dichroism (CD) Analysis for Conductive β-Peptide/SWNT Complex

Figure 10:
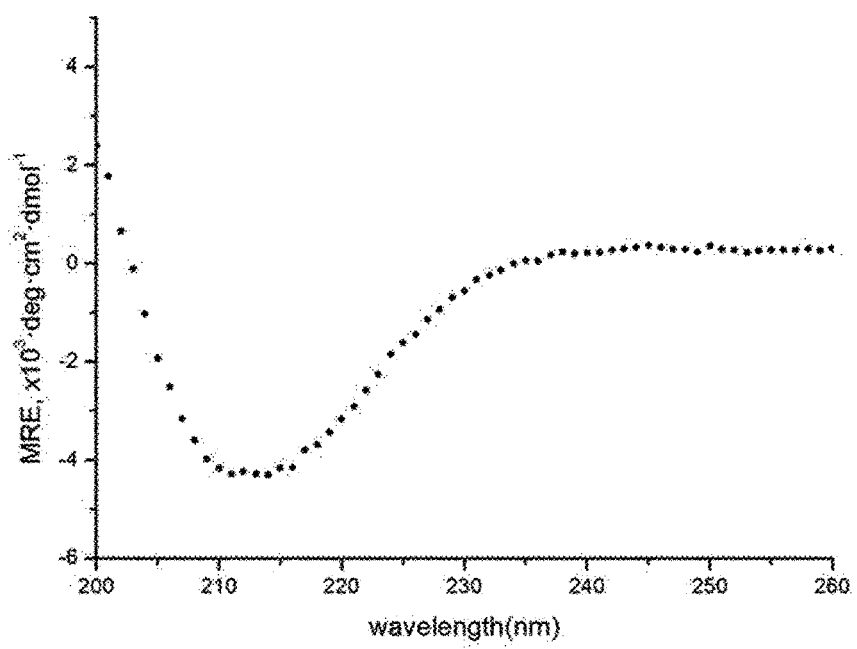
FIG. 10 shows results of analyzing the β-peptide/carbon nanotube complex using a circular dichroism (CD) spectroscopy.

An ellipticity of β-peptide was measured using a circular dichroism spectrometer (J-810 model of JASCO corporation) to confirm that the β-peptide forms a stable α-helical structure when it forms a complex with SWNT. Measurement of the CD was conducted by filling a cuvette having a tunnel length of 1 mm with a 100 µM concentration β-peptide/SWNT complex solution to obtain a spectrum from 250 nm to 190 nm, and then a mole ellipticity was calculated for each amino acid residue. At about 214 nm, the CD showed a minimum value, which suggests that in the β-peptide/SWNT complex, the β-peptide retained its original helical shape even when the β-peptide was covering the SWNT (FIG. 10).

Example 4: Preparation a Conductive Peptide Gel

Figure 11:
FIG. 11 shows a photograph of a biocompatible conductive protein gel prepared according to the present disclosure.

The synthesized β-peptide/SWNT was concentrated for 10 folds using a centrifugal separation filter apparatus (Microcon-30 kDa, MRCF0R030). In this example, 1 mL of β-peptide/SWNT solution was concentrated to 100 µL. The concentrated β-peptide/SWNT solution was mixed with a 100 µL of 20 mg/mL β-peptide solution having increased viscosity due to fibrolization in a pH 7.4 Tris-HCL buffer solution, and then kept at room temperature for one day. In order to adjust the final concentration to 20 mg/mL, a reconcentration process was conducted twice using the centrifugal separation filter apparatus, finally to yield a conductive peptide gel (FIG. 11).

Measurement of Conductivity of Conductive Peptide Gel

Figure 12:
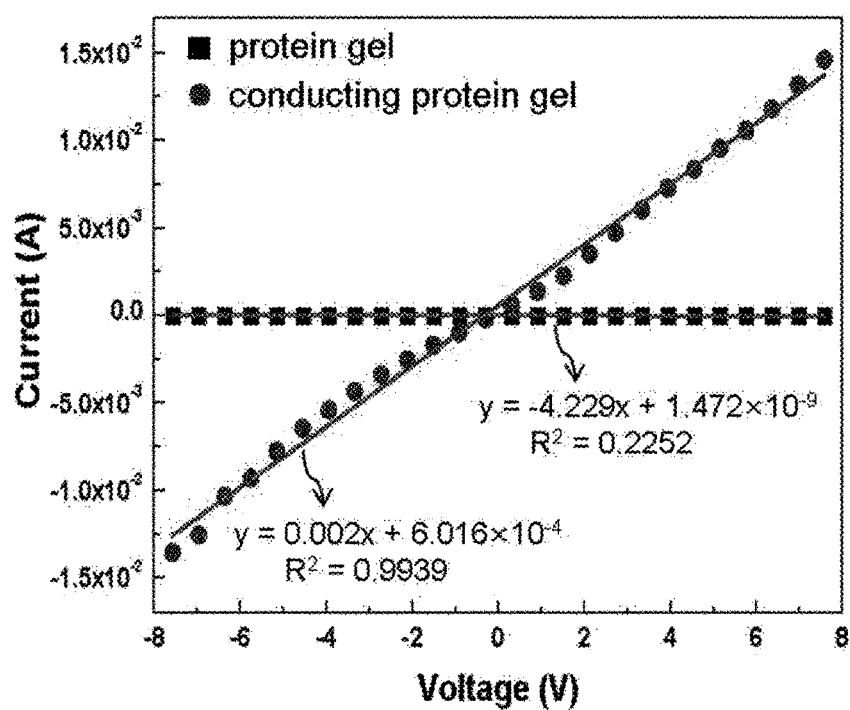
FIG. 12 shows results of measuring and analyzing conductivities of conductive protein gels prepared according to the present disclosure.

The conductivity of the conductive peptide gel prepared in example 4 was measured by dropping 100 µL of the peptide gel between gold electrodes. The conductivities of the peptide gel and the conductive peptide gel were compared and, the conductivity of the conductive peptide gel was confirmed as I-V curve was measured (FIG. 12). Therefore, the conductive peptide gel of the present disclosure can be utilized as a conductive biomaterial in various application fields such as neurological recovery medicine, drug delivery system, conductive flexible coating, tissue engineering, optogenetics and the like.

While this invention has been described in connection with what is presently considered to be practical embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

What is claimed is:

1. A biocompatible protein comprising an amino acid sequence of Lys-X-Lys-Glu-X-Phe-Phe-X-Lys-Glu-X-Phe-Phe-X-Lys-Glu-X-Tyr (SEQ ID NO: 28), wherein each instance of X is independently a hydrophobic amino acid.

2. A biocompatible protein comprising an amino acid sequence of Lys-X-Lys-(Glu-X-Phe-Phe-X-Lys)$_n$-Glu-X-Tyr (1≤n≤9, corresponding to SEQ ID NOs: 25, 24, 23, 22, 21, 20, 19, 18, and 17, respectively), wherein each instance of X is independently a hydrophobic amino acid.

3. The biocompatible protein according to claim 1, wherein the amino acid sequence comprises (Lys-X-Lys-Glu-X-Phe-Phe-X-Lys-Glu-X-Phe-Phe-X-Lys-Glu-X-Tyr)$_n$ (1≤n≤3, corresponding to SEQ ID NOs: 28, 27, and 26, respectively) by repetition.

4. The biocompatible protein according to claim 1, wherein lysine (K) is added to an N-terminus or C-terminus of the amino acid sequence.

5. The biocompatible protein according to claim 1, wherein the amino acid sequence consists of β-amino acids.

6. The biocompatible protein according to claim 1, wherein the amino acid sequence comprises any one or more of SEQ ID NO:2 to SEQ ID NO:11.

7. The biocompatible protein according to claim 2, wherein the amino acid sequence comprises any one or more of SEQ ID NO:1, SEQ ID NO:2, SEQ ID NO:12, and SEQ ID NO:13.

8. The biocompatible protein according to claim 1, wherein the biocompatible protein is not degraded by an enzyme.

9. The biocompatible protein according to claim 8, wherein the enzyme is a protease that comprises one or more of trypsin, chymotrypsin, and subtilisin.

10. A biocompatible protein gel that comprises the biocompatible protein of claim 1.

11. The biocompatible protein gel according to claim 10, wherein the biocompatible protein comprises an amino acid sequence consisting of β-amino acids.

12. The biocompatible protein gel according to claim 10, wherein the biocompatible protein comprises any one or more of SEQ ID NO:1 to SEQ ID NO:13.

13. A biocompatible conductive protein gel comprising a complex of the biocompatible protein of claim 1 and a conductive nano material.

14. The biocompatible conductive protein gel according to claim 13, wherein the biocompatible protein comprises an amino acid sequence consisting of β-amino acids.

15. The biocompatible conductive protein gel according to claim 13, wherein the biocompatible protein comprises any one or more of SEQ ID NO:1 to SEQ ID NO:13.

16. The biocompatible conductive protein gel according to claim 13, wherein the conductive nano material comprises any one or more of a carbon nanotube (CNT), fullerene ($C_{60}$), conductive polymer nanowire, conductive polymer nanotube, conductive polymer nanoparticle, metal nanowire, and metal nanoparticle.

17. The biocompatible conductive protein gel according to claim 16, wherein the carbon nanotube is a single-walled carbon nanotube or multi-walled carbon nanotube.

* * * * *